(12) United States Patent
Nakao

(10) Patent No.: US 8,619,254 B2
(45) Date of Patent: Dec. 31, 2013

(54) ANALYSIS TOOL AND MICROANALYSIS SYSTEM

(75) Inventor: Tomoki Nakao, Saitama (JP)

(73) Assignee: Enplas Corporation, Saitama (JP)

( * ) Notice: Subject to any disclaimer, the term of this patent is extended or adjusted under 35 U.S.C. 154(b) by 269 days.

(21) Appl. No.: 13/112,511

(22) Filed: May 20, 2011

(65) Prior Publication Data

US 2011/0285990 A1    Nov. 24, 2011

(30) Foreign Application Priority Data

May 21, 2010    (JP) .................................. 2010-117552

(51) Int. Cl.
*G01N 1/10*    (2006.01)
*G01N 35/00*    (2006.01)

(52) U.S. Cl.
USPC ........... 356/246; 356/440; 422/505; 422/502; 422/504

(58) Field of Classification Search
USPC ........... 356/244, 246, 432–440; 422/50, 407, 422/68.1, 500, 502, 62; 137/177, 833; 257/40, 414; 402/505, 504, 400, 63, 81
See application file for complete search history.

(56) References Cited

U.S. PATENT DOCUMENTS

| | | | | |
|---|---|---|---|---|
| 6,383,452 B1* | 5/2002 | Miyake et al. | ................... | 422/63 |
| 8,153,059 B2* | 4/2012 | Trieu et al. | ...................... | 422/50 |
| 8,362,468 B2* | 1/2013 | Ono et al. | ......................... | 257/40 |
| 2004/0200724 A1* | 10/2004 | Fujii et al. | ...................... | 204/601 |
| 2006/0213291 A1* | 9/2006 | Sando et al. | ................. | 73/866.5 |
| 2006/0239862 A1* | 10/2006 | Nakajima et al. | ............. | 422/100 |
| 2008/0135484 A1* | 6/2008 | Hammer | ........................ | 210/656 |
| 2010/0166612 A1* | 7/2010 | Lehto | .......................... | 422/82.05 |
| 2011/0045993 A1* | 2/2011 | Kent et al. | ......................... | 506/7 |

FOREIGN PATENT DOCUMENTS

JP    2006-115742 A    5/2006
JP    2008-238090 A    10/2008

* cited by examiner

*Primary Examiner* — Hoa Pham
(74) *Attorney, Agent, or Firm* — Washida IP Group

(57) ABSTRACT

In a case of generating a main body of an analysis tool and a micro flow path chip as separate components, to obtain an accurate sample analysis result and to accurately adjust fluid temperature inside the micro flow path chip without damaging an analytical light receiving section of the micro flow path chip. In analysis tool body (10) that detachably holds micro flow path chip (30) in a fixed manner, notch section (21) is formed in mount surface (13) onto which micro flow path chip (30) is to be mounted. Notch section (21) is formed in a predetermined range including a part corresponding to optical path L of light emitted from a lens of optical unit (60) in a state where analysis tool (1) is arranged on heat block (50).

4 Claims, 6 Drawing Sheets

ANALYSIS TOOL AND MICROANALYSIS SYSTEM

CROSS REFERENCE TO RELATED APPLICATIONS

The disclosure of Japanese Patent Application No. 2010-117552, filed on May 21, 2010, including the specification, drawings and abstract, is incorporated herein by reference in its entirety.

TECHNICAL FIELD

The present invention relates to an analysis tool including a micro flow path chip made of resin and a microanalysis system provided with the same.

BACKGROUND ART

In the recent years, in a scientific field of biochemistry, analytical chemistry and the like or in a medical field, a microanalysis system is used for performing an accurate and high-speed test analysis of minor substances such as protein or nucleic acid (e.g. DNA).

As one of such microanalysis systems, there is a system in which a micro flow path with a width and depth of about a few tenth to 200 μm is formed inside an analysis tool, a migrating solution (buffer solution, gel) is filled in the flow path, a sample is injected from one end of the flow path onto which a voltage is applied, and an analysis is performed by causing electrophoresis of the sample.

In the analysis of the sample as above, a method of arranging the analysis tool including the micro flow path in an analysis device including an optical unit capable of receiving and emitting analytical light, causing electrophoresis of the sample, radiating light to a predetermined position in the flow path, and observing a fluorescent wavelength emitted by the sample in the flow path is known.

Further, in order to maintain the fluid inside the micro flow path to be at a predetermined temperature, a technique of arranging a heater as a heat exchanging device in the vicinity of the flow path in the analysis tool is also known (cf. patent literature 1).

As a method of adjusting the temperature of the fluid inside the micro flow path, there is also a technique of adjusting the fluid temperature inside the micro flow path by holding the analysis tool (substrate) including the micro flow path with two heat blocks and controlling temperatures of these heat blocks (cf. patent literature 2).

Meanwhile, recently, there is a major trend of manufacturing the analysis tool including the micro flow path with resin. By using resin as the material of the analysis tool, a cheap mass-production can be implemented compared to a case of manufacturing the aforementioned analysis tool with glass.

Further, compared to those made of glass, the analysis tool including the micro flow path and made of resin can easily form a complicated shape; thus, a freedom of design can be increased.

CITATION LIST

Patent Literature

PTL 1: Japanese Patent Application Publication No. 2008-238090

PTL 2: Japanese Patent Application Publication No. 2006-115742

SUMMARY OF INVENTION

Technical Problem

However, in a case where the heater is integrally formed with a main body of the analysis tool including the micro flow path, an increase in an analysis cost is induced due to the heater being disposed with the analysis tool each time after a one-time use. In order to reduce the cost, it is preferable to provide the heat exchanging device such as the optical unit, the heat block and the like in the analysis device as separate components from the analysis tool.

Further, in order to reduce the cost, it is required to limit a part to be disposed in the analysis tool installed in the analysis device to a minimum necessary part that is the micro flow path part, and to enable the main body of the analysis tool to be used repeatedly.

In a microanalysis system with such a configuration, a problem is to be able to achieve a high heat conductivity for the fluid inside the micro flow path chip even in the case where the heat block and the micro flow path chip are formed as separate components.

Further, in attaching the micro flow path chip in the main body of the analysis tool, there is a risk of damaging a bottom surface of the micro flow path chip by the bottom surface of the micro flow path chip being rubbed against the main body of the analysis tool, and a new problem that a highly accurate photoanalysis cannot be performed may occur.

The present invention has been made in view of the foregoing, and it is an object of the present invention to provide an analysis tool and a microanalysis system that are capable of obtaining an accurate sample analysis result without damaging an analytical light receiving section of a micro flow path chip and capable of accurately adjusting fluid temperature inside the micro flow path chip in a case of generating a main body of the analysis tool and the micro flow path chip as separate components.

Solution to Problem

An analysis tool of the present invention employs an configuration of an analysis tool used in an analysis system provided with the analysis tool including a micro flow path, a heat exchanging block capable of heating and cooling and an optical unit capable of emitting and receiving analytical light, the system in which light is radiated onto a sample located at a predetermined position in the micro flow path in a state where temperature of the micro flow path is controlled to be at a predetermined value and the analytical light from the sample is detected, the analysis tool including: a micro flow path chip made of resin and in which the micro flow path is formed in an inside; and a main body of the analysis tool that holds the micro flow path chip in a detachably attached manner, wherein the micro flow path is formed so as to pass through an optical path of the light radiated from an analytical light emitting section of the optical unit in a state where the analysis tool is arranged on the heat exchanging block, and on a mount surface of the main body of the analysis tool onto which the micro flow path chip is to be mounted, a clearance section for preventing contact with the micro flow path chip is performed in a predetermined range including the optical path portion in the state where the analysis tool is arranged on the heat exchanging block.

The microanalysis system of the present invention employs a configuration being provided with the above analysis tool.

Advantageous Effects of Invention

According to the present invention, in the case of generating the main body of the analysis tool and the micro flow path chip as separate components, the accurate sample analysis result can be obtained and the fluid temperature inside the micro flow path chip can be adjusted accurately. Further, by forming the main body of the analysis tool and the micro flow path chip as separate components, the part to be disposed can be kept to the minimum and the cost can be reduced; and by preparing main bodies of the analysis tools respectively adapted for plural kinds of analysis devices, the micro flow path chip can be mutually used therein.

DESCRIPTION OF EMBODIMENTS

Embodiments of the present invention of the present invention will be described below in detail with reference to the accompanying drawings.

[Configuration of Analysis Tool]

Figure 1:
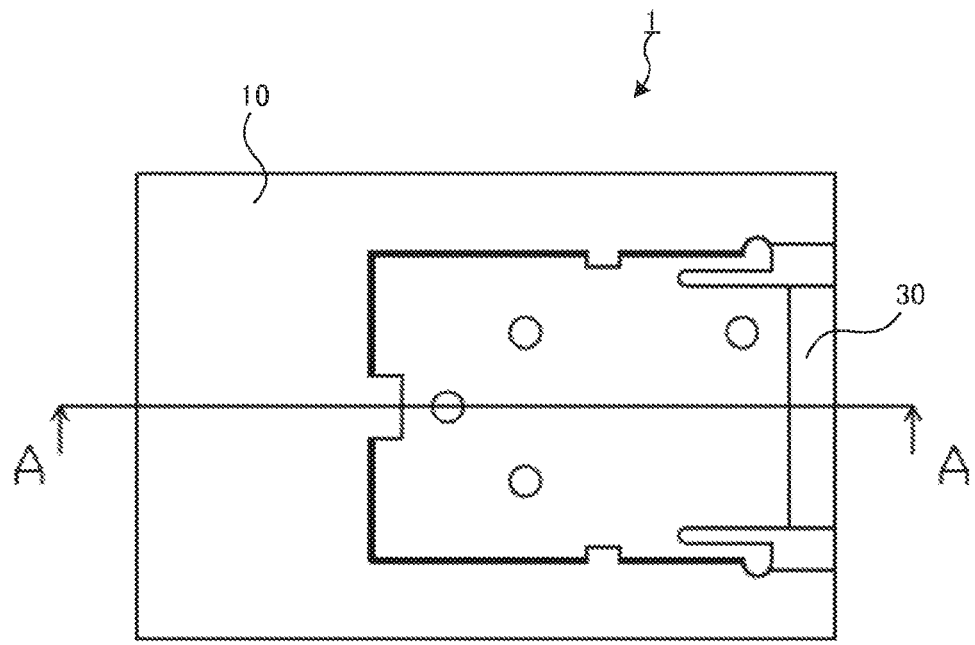
FIG. 1 is a plan view of an analysis tool of an embodiment of the present invention.
Figure 2:
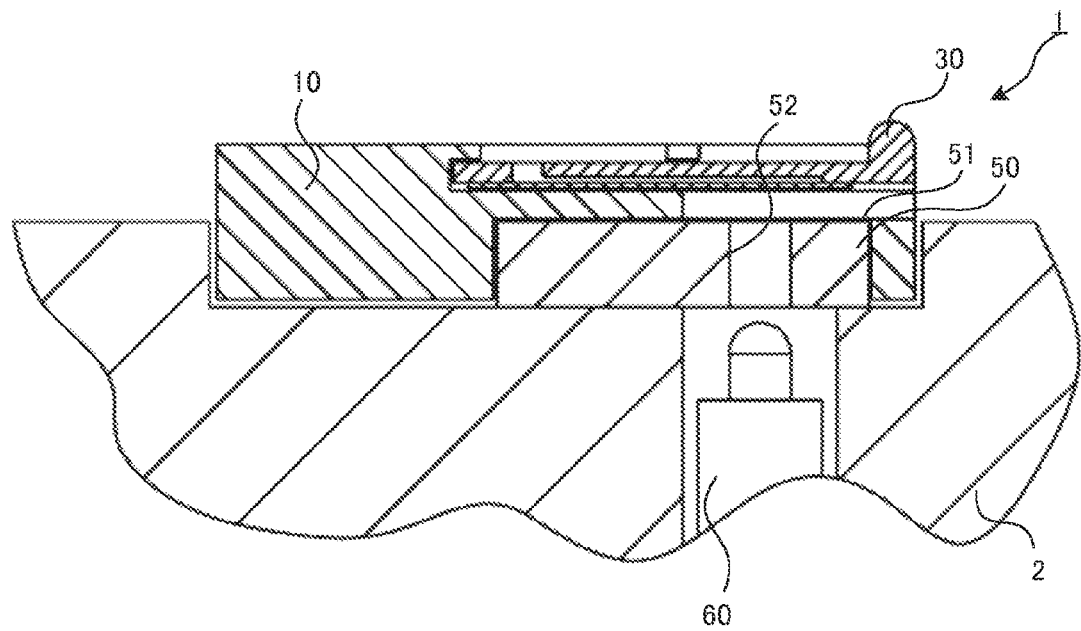
FIG. 2 is a cross-sectional view taken along A-A of FIG. 1.

FIG. 1 is a plan view of an analysis tool of an embodiment of the present invention. FIG. 2 is a cross-sectional view taken along A-A of FIG. 1. Note that in FIG. 2, a configuration of a part of a microanalysis system is also shown.

As shown in FIG. 1 and FIG. 2, analysis tool 1 is configured of main body of analysis tool (also referred to as "analysis tool body") 10 and micro flow path chip 30. Micro flow path chip 30 is detachably attached to analysis tool body 10. Analysis tool body 10 retains attached micro flow path chip 30 in a fixed manner. Note that details of analysis tool body 10 and micro flow path chip 30 will be described later.

Main body of analysis device 2 includes heat block 50 and optical unit 60. Upon performing a sample analysis, analysis tool 1 is arranged on heat block 50 of main body of microanalysis device 2.

Heat block 50 makes contact with analysis tool body 10 at its upper surface 51 (upper end surface in FIG. 2), and transmits heat to micro flow path chip 30 via analysis tool body 10 so as to maintain micro flow path chip 30 at a substantially constant temperature.

In heat block 50, through-hole 52 through which light radiated from optical unit 60 and fluorescent light emitted from the sample inside micro flow path chip 30 pass is formed.

Optical unit 60 emits the light to be radiated onto micro flow path chip 30 and receives the analytical light. The light emitted from a lens of optical unit 60 condenses toward the sample inside micro flow path chip 30 by passing through through-hole 52, and the fluorescent light emitted from the sample inside micro flow path chip 30 is received by the lens of optical unit 60 by passing through through-hole 52.

[Configuration of Main Body of Analysis Tool]

Figure 3:
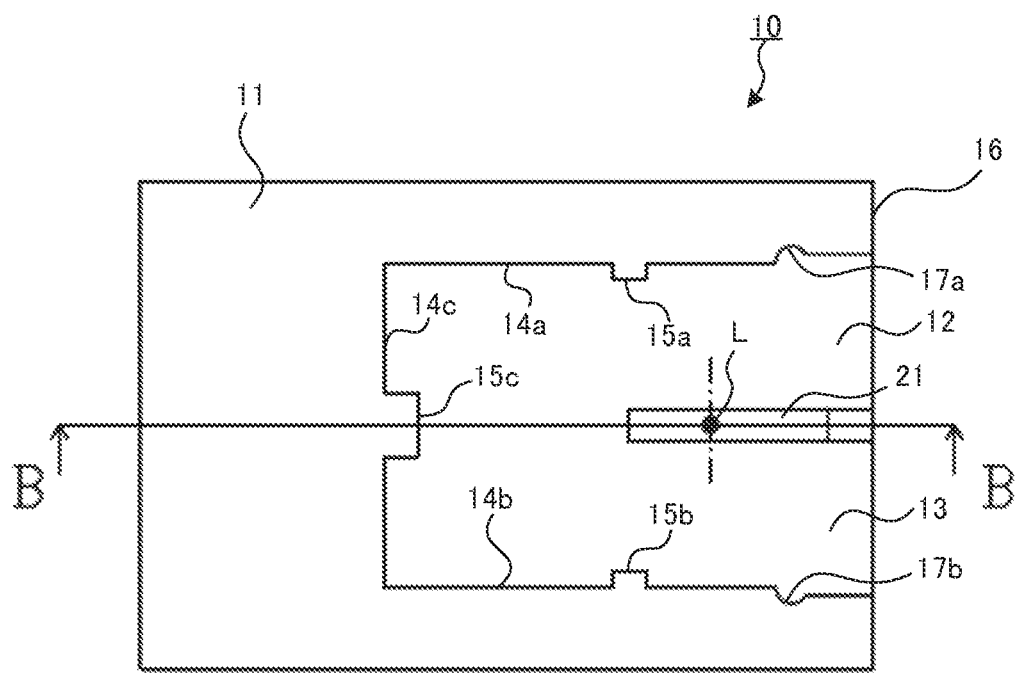
FIG. 3 is a plan view of an analysis tool of an embodiment of the present invention.
Figure 4:
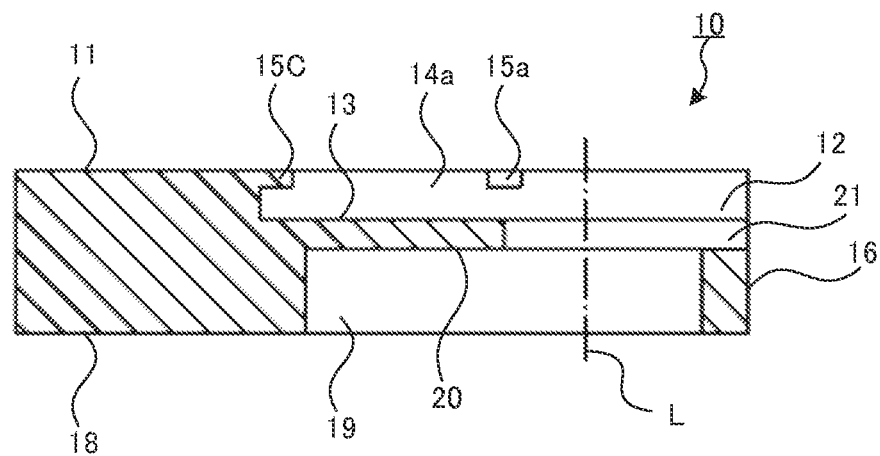
FIG. 4 is a cross-sectional view taken along B-B of FIG. 3.

FIG. 3 is a plan view of the analysis tool of the embodiment of the present invention. Further, FIG. 4 is a cross-sectional view taken along B-B of FIG. 3.

Analysis tool body 10 has an outer shape that is substantially a rectangular parallelepiped, and is formed of resin material such as PMMA (polymethylmethacrylate), PC (polycarbonate), EP (epoxy resin) and the like.

On upper surface 11 (upper end surface in FIG. 4) side of analysis tool body 10, attachment section 12 for attaching micro flow path chip 30 is formed. Attachment section 12 includes mount surface 13 at a predetermined depth from upper surface 11 for mounting micro flow path chip 30. Mount surface 13 is formed with a size in which its width is somewhat wider than a width of micro flow path chip 30 and its depth is substantially the same as a length of micro flow path chip 30.

Inner surfaces 14a, 14b of attachment section 12 serves as a guide upon attaching micro flow path chip 30 to analysis tool body 10. Each of inner surfaces 14a, 14b, 14c of attachment section 12 is formed with a protrusion 15a, 15b, 15c for holding micro flow path chip 30. Further, in inner surfaces 14a, 14b, concave sections 17a, 17b for fixing micro flow path chip 30 by engaging with convex sections 39a, 39b of micro flow path chip 30 (cf. FIG. 5) are formed on left side surface 16 (left end surface in FIG. 4) side.

At lower surface 18 (lower end surface in FIG. 4, opposite to upper surface 11) side of analysis tool body 10, counterbore section 19 is formed. Bottom surface 20 of counterbore section 19 is parallel to mount surface 13, somewhat larger than upper surface 51 of heat block 50, and makes contact with upper surface 51 of heat block 50 in the sample analysis. Analysis tool body 10 receives heat from heat block 50 by bottom surface 20 of counterbore section 19, and transmits the heat to micro flow path chip 30 from mount surface 13.

At a center part of left side surface 16 of analysis tool body 10, notch section 21 is formed. Notch section 21 is formed to include a part corresponding to an optical path of the light radiated from the lens of optical unit 60 (hereinafter referred to simply as "optical path") L when analysis tool 1 is arranged on heat block 50. By forming notch section 21 so as to include the part corresponding to optical path L, a part corresponding to optical path L at bottom surface 42 of micro flow path chip 30 (cf. FIG. 6) can be prevented from being damaged by being rubbed against mount surface 13.

Further, by making notch section 21 at a minimum necessary length, a contacting area of mount surface 13 and bottom surface 42 of micro flow path chip 30 can be made larger, and the heat from heat block 50 can sufficiently be transmitted to micro flow path chip 30 via analysis tool body 10.

A thickness of a plate-shaped section from bottom surface 20 of counterbore section 19 serving as a heat transmitting section to mount surface 13 can be changed in accordance with a position of heat block 50 of main body of microanalysis device 2 to which analysis tool body 10 is attached, and adjustment can be made such that a position of condensation of the light emitted from optical unit 60 matches to be inside an analytical flow path of micro flow path chip 30.

[Configuration of Micro Flow Path Chip]

Figure 5:
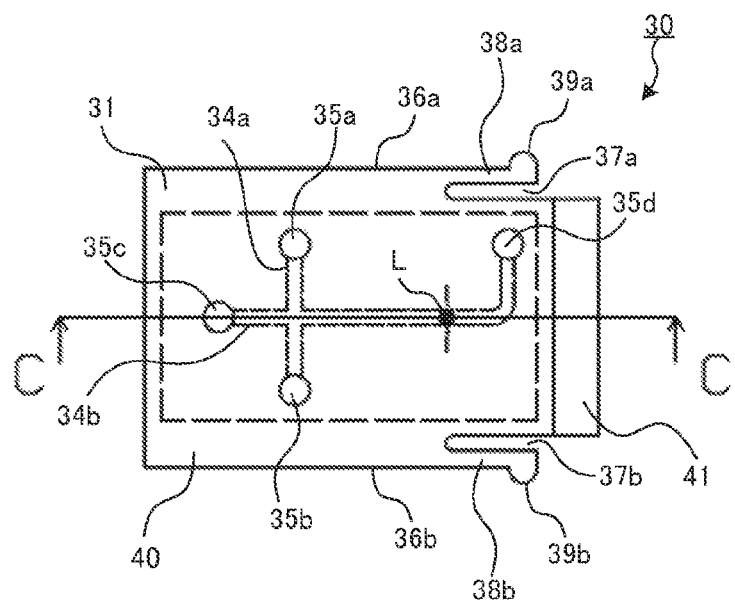
FIG. 5 is a plan view of a micro flow path chip of an analysis tool of an embodiment of the present invention.
Figure 6:
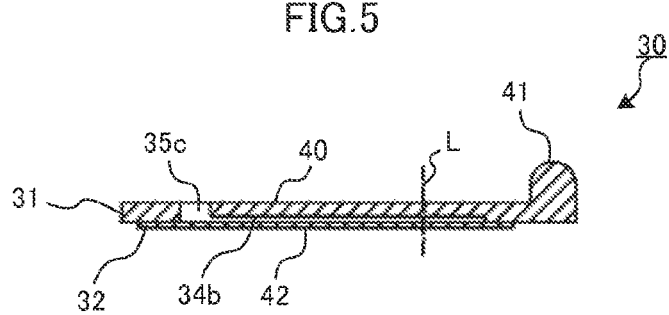
FIG. 6 is a cross-sectional view taken along C-C of FIG. 5.
Figure 7:
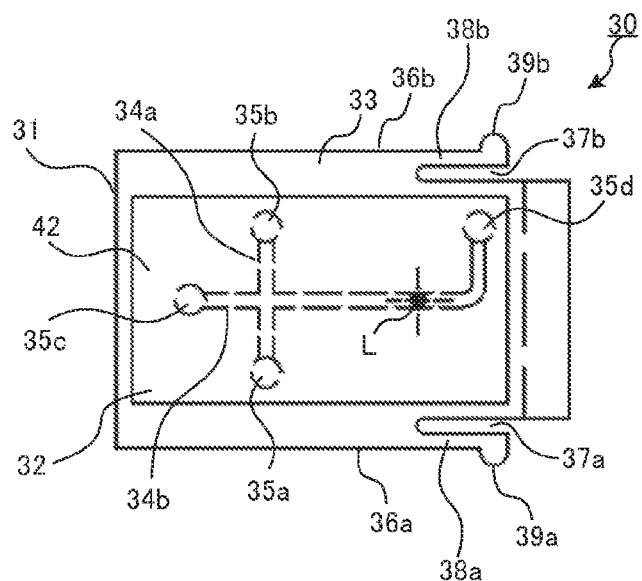
FIG. 7 is a bottom view of a micro flow path chip of an analysis tool of an embodiment of the present invention.

FIG. 5 is a plan view of a micro flow path chip of an embodiment of the present invention. Further, FIG. 6 is a cross-sectional view taken along C-C of FIG. 5. Further, FIG. 7 is a bottom view of the micro flow path chip of the embodiment of the present invention.

Micro flow path chip 30 is configured of flat plate 31 with a thickness of about 1 mm and film 32 with a thickness of about 100 µm. Flat plate 31 and film 32 are formed of transparent resin material such as PMMA (polymethylmethacrylate), PC (polycarbonate), EP (epoxy resin) and the like.

In flat plate 31, elongated and narrow flow paths 34a, 34b are formed on surface (lower surface) 33 opposing film 32 in a manner that the two intersect one another at an intermediate portion. Flow paths 34a, 34b respectively have a substantially rectangular cross section with each edge having a length (width and depth) of about a few tenth µm. Further, flow path 34b is formed such that analysis tool 1 passes over optical path L upon being arranged on heat block 50.

In flat plate 31, at both ends of each of flow paths 34a, 34b, through-holes (injection openings) 35a, 35b, 35c, 35d having substantially round cross sections and opening toward an outside are formed. Each of through-holes 35a, 35b, 35c, 35d has a diameter of a few hundred µm to a few mm, and has a size large enough to function as an injection opening or an ejection opening for an organic solvent and a solution of analysis target.

Film 32 is adhered to lower surface 33 of flat plate 31 by an adhesion using a transparent organic adhesive or a thermocompression bonding and the like so as to cover at least flow paths 34a, 34b and through-holes 35a, 35b, 35c, 35d.

By forming slits 37a, 37b at both end portions on side surface 36a of flat plate 31, plate springs 38a, 38b are formed on side surfaces 36b, 36c. Further, at distal ends of plate springs 38a, 38b, convex sections 39a, 39b for engaging with concave sections 17a, 17b of analysis tool body 10 are formed.

Further, knob section 41 in which side surface 36a side of upper surface 40 (opposite surface of lower surface 33) of flat plate 31 is protruded is formed in flat plate 31. By forming knob section 41, an examiner can pinch this knob section 41 with his/her fingers, and can easily attach micro flow path chip 30 to analysis tool body 10. Further, due to this, since the examiner can attach micro flow path chip 30 to analysis tool body 10 without touching bottom surface 42 of micro flow path chip 30 (film 32), the examiner does not dirty or damage bottom surface 42.

Further, by forming notch section 21 in analysis tool body 10, the part of bottom surface 42 of micro flow path chip 30 corresponding to optical path L is not damaged by being rubbed against mount surface 13 upon attaching micro flow path chip 30 to analysis tool body 10. Accordingly, the light radiated from the lens of optical unit 60 to the sample and the fluorescent light from the sample are prevented from being reflected irregularly in micro flow path chip 30.

[Process of Sample Analysis]

In conducting the sample analysis, first, the examiner attaches micro flow path chip 30 to analysis tool body 10. Specifically, the examiner holds analysis tool body 10 with one hand and pinches knob section 41 of micro flow path chip 30 with the fingers of the other hand, places micro flow path chip 30 on mount surface 13 of analysis tool body 10, and presses the distal end side (opposite side of knob section 41) of micro flow path chip 30 by passing it under protrusions 15a, 15b until concave sections 17a, 17b and convex sections 39a, 39b are engaged.

Next, the examiner fills migrating solution in flow paths 34a, 34b of micro flow path chip 30, and injects the sample from through-hole (injection opening) 35a.

Next, the examiner arranges analysis tool 1 on heat block 50, and causes temperature of micro flow path chip 30 to be at a predetermined value by controlling temperature of heat block 50.

Next, the examiner applies negative (−) voltage to through-holes 35a, 35c, 35d, and applies positive (+) voltage to through-hole 35b. Due to this, electrophoresis of the sample is caused within flow path 34a from through-hole 35a toward through-hole 35b.

Then, after a predetermined time has elapsed, the examiner applies negative (−) voltage to through-holes 35a, 35b, 35c, and applies positive (+) voltage to through-hole 35d. Due to this, only the sample that had been at an intersecting portion of flow path 34a and flow path 34b is cut out, and electrophoresis thereof is caused within flow path 34a toward through-hole 35d. Further, the sample inside flow path 34b is separated by a difference in a speed of electrophoresis of each molecular mass.

Then, after a predetermined time has elapsed, the examiner radiates the light to the sample from the lens of optical unit 60, and observes fluorescent wavelength of the sample. By measuring a fluorescence intensity and fluorescence detecting time, a result of electrophoresis can be obtained.

EFFECTS OF THE EMBODIMENT

As described above, according to the present embodiment, by forming analysis tool body 10 and micro flow path chip 30 as separate components, the part to be disposed can be kept to the minimum and the cost can be reduced; and by preparing analysis tool bodies 10 respectively adapted for plural kinds of analysis devices, micro flow path chip 30 can be mutually used therein.

Further, by forming notch section 21 so as to include the part corresponding to optical path L, the part of bottom surface 42 of micro flow path chip 30 corresponding to optical path L can be prevented from being damaged. Accordingly, since the light radiated from the lens of optical unit 60 to the sample and the fluorescent light from the sample are prevented from being reflected irregularly in micro flow path chip 30, an accurate sample analysis result can be obtained.

Further, by forming notch section 21 so as to include the part corresponding to optical path L, since the analytical light does not go through analysis tool body 10 that is formed of a material having an intrinsic fluorescence property, a background of detection light in optical unit 60 can be kept low.

Further, by making notch section 21 with the minimum necessary width and length, the contacting area of mount surface 13 and bottom surface 42 of micro flow path chip 30 can be made larger; thus the heat from heat block 50 can sufficiently be transmitted to micro flow path chip 30 via analysis tool body 10, and the temperature of micro flow path chip 30 can be adjusted accurately.

Note that, in the present embodiment, micro flow path chip 30 for electrophoresis purposes has been given as an example, however, the present invention is not limited hereto, and it can be adapted to any micro flow path chip so long as it is a micro flow path chip in which a part of a flow path is used as a photoanalysis section.

Further, in the present embodiment, a case in which the analytical light from the sample is the fluorescent light has been given as an example, however, the present invention is not limited hereto, and it can be adapted to cases in which an analytical light emitting section and an analytical light receiving section of optical unit 60 are arranged facing one another with the photoanalysis section of the micro flow path chip interposed therebetween, and performing absorption spectrophotometry by light that had passed through the sample in the micro flow path chip.

Further, in the present embodiment, a case in which analysis tool body 10 and micro flow path chip 30 are formed of the same material has been given as an example, however, the present invention is not limited hereto, and analysis tool body 10 that is not a disposable component can be formed of a material with high heat conductivity. Accordingly, by forming analysis tool body 10 and micro flow path chip 30 with different materials, it becomes possible to improve the accuracy of the analysis as well as to reduce the analysis cost.

[Variation 1]

Figure 8:
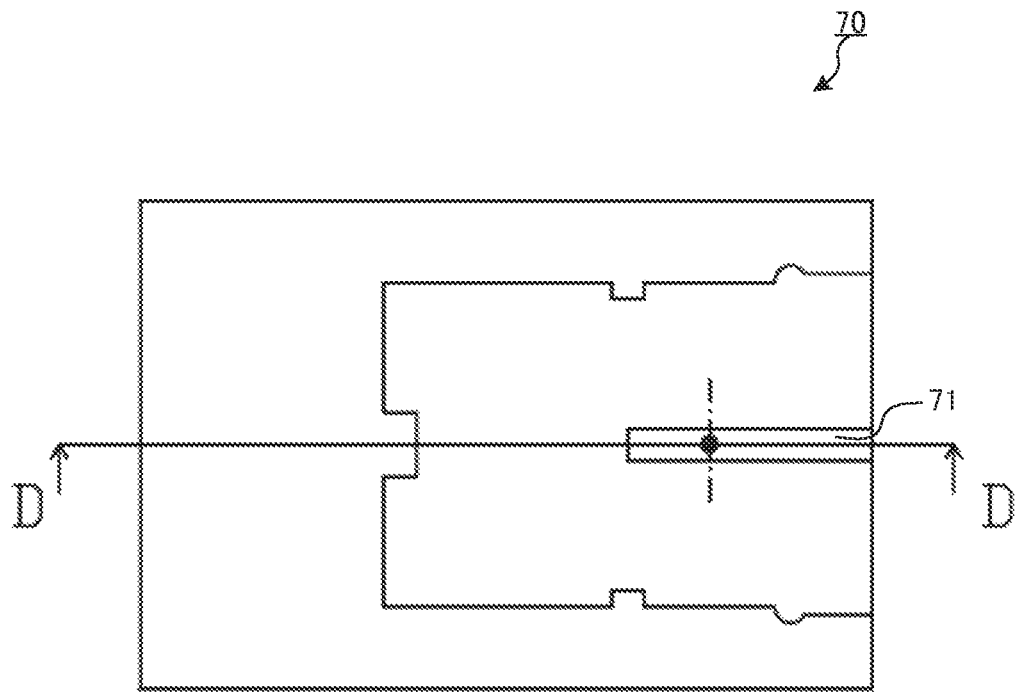
FIG. 8 is a plan view of a main body of an analysis tool of variation 1 of an embodiment of the present invention.
Figure 9:
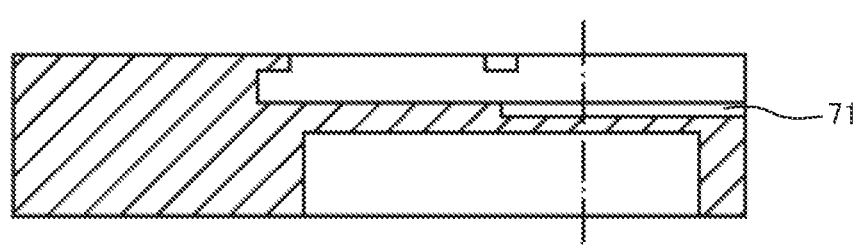
FIG. 9 is a cross-sectional view taken along D-D of FIG. 7.

Note that, in the present embodiment, as shown in FIG. 8 and FIG. 9, as an alternative of notch section 21, by forming concave section 71 on mount surface 13 of analysis tool body 70, the part of bottom surface 42 of micro flow path chip 30 corresponding to optical path L is prevented from being damaged.

FIG. 8 is a plan view of the main body of the analysis tool of variation 1 of the embodiment of the present invention, and FIG. 9 is a cross-sectional view taken along D-D of FIG. 8. Analysis tool body 70 shown in FIG. 8 and FIG. 9 differ in that concave section 71 is formed instead of notch section 21 compared to analysis tool body 10 of FIG. 3 and FIG. 4.

Accordingly, by forming concave section 71, compared to the case of forming notch section 21, although the light radiated to the sample from the lens of optical unit 60 and the fluorescent light from the sample causes a minor intrinsic fluorescence in analysis tool body 70, this is not a problem so long as no influence is imposed on the analysis accuracy, and it has an advantage that analysis tool body 70 becomes less prone to deformation.

[Variation 2]

Further, in the present embodiment, there is no specific limitation as to a method by which a main body of an analysis tool and a micro flow path chip are engaged.

Figure 10:
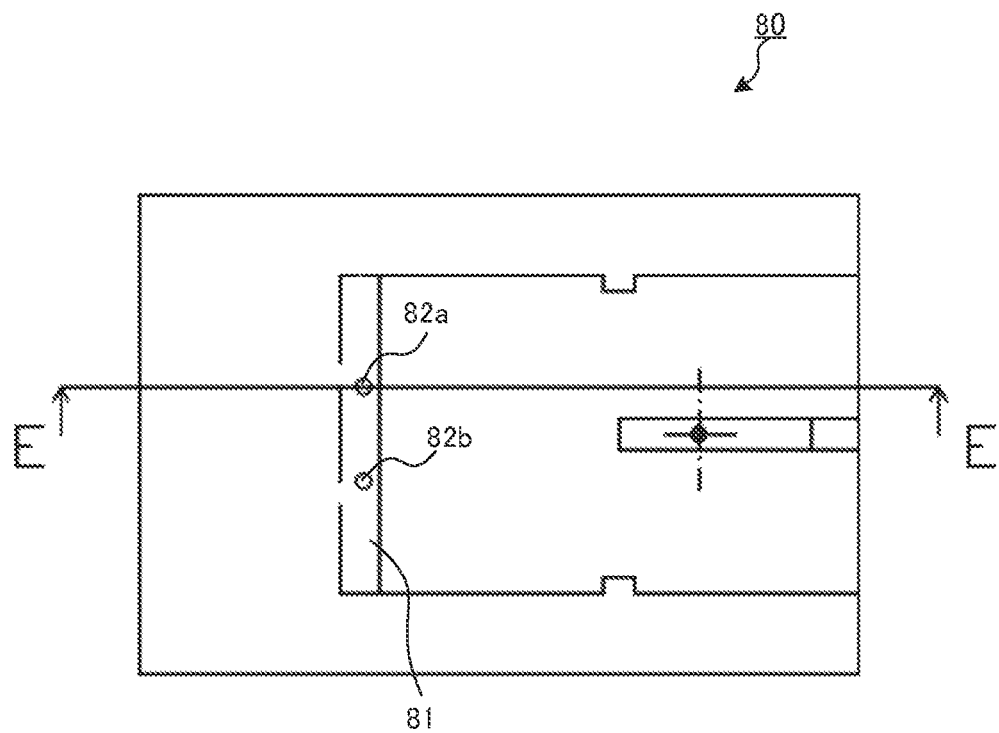
FIG. 10 is a plan view of a main body of an analysis tool of variation 2 of an embodiment of the present invention.
Figure 11:
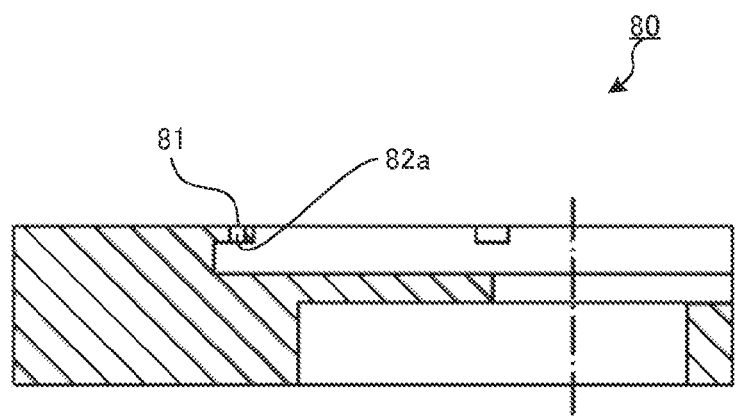
FIG. 11 is a cross-sectional view taken along E-E of FIG. 10.
Figure 12:
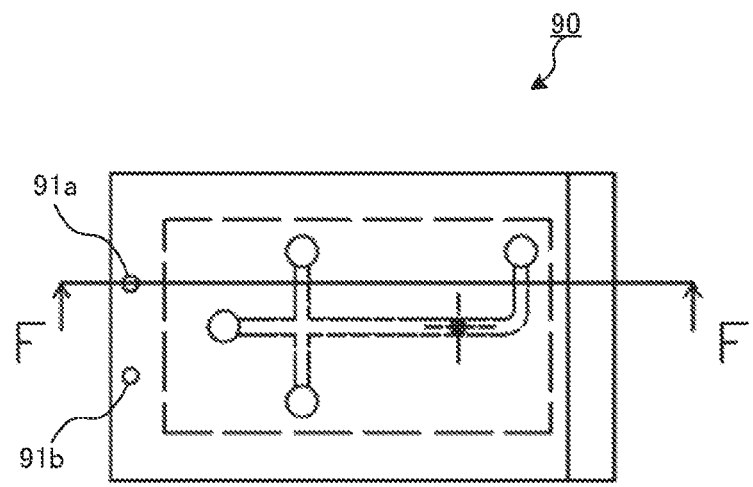
FIG. 12 is a plan view of a micro flow path chip of the analysis tool of variation 2 of the embodiment of the present invention.
Figure 13:
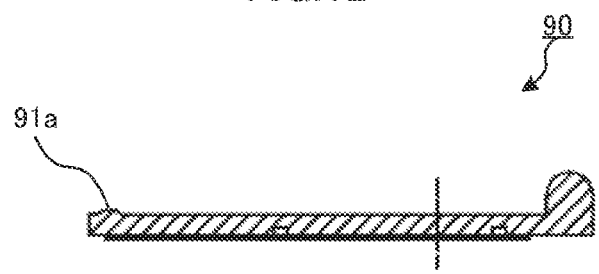
FIG. 13 is a cross-sectional view taken along F-F of FIG. 12.

FIG. 10 is a plan view of the main body of the analysis tool of variation 2 of the embodiment of the present invention. Further, FIG. 11 is a cross-sectional view taken along E-E of FIG. 10. Further, FIG. 12 is a plan view of the micro flow path chip of the analysis tool of variation 2 of the embodiment of the present invention. Further, FIG. 13 is a cross-sectional view taken along F-F of FIG. 12. Further, FIG. 14 is a bottom view of the micro flow path chip of the analysis tool of variation 2 of the embodiment of the present invention.

Analysis tool body 80 shown in FIG. 10 and FIG. 11 is not provided with protrusion 15c and concave sections 17a, 17b, but instead, retaining section 81 and through-holes 82a, 82b are formed compared to analysis tool body 10 of FIG. 3 and FIG. 4.

Figure 14:
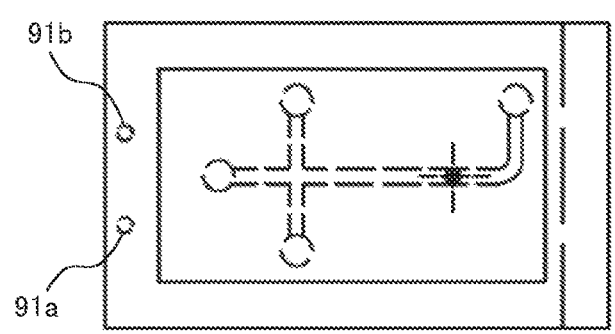
FIG. 14 is a bottom view of the micro flow path chip of the analysis tool of variation 2 of the embodiment of the present invention.

Micro flow path chip 90 shown in FIG. 12 to FIG. 14 is not provided with plate springs 38a, 38b and convex sections 39a, 39b, but instead, convex sections 91a, 91b are formed compared to micro flow path chip 30 shown in FIG. 5 to FIG. 7.

By engaging through-holes 82a, 82b of analysis tool body 80 and convex sections 91a, 91b of micro flow path chip 90, micro flow path chip 90 can be retained to analysis tool body 80 in a retained manner.

INDUSTRIAL APPLICABILITY

The analysis tool and the microanalysis system of the present invention can be used in devices used for performing accurate and high-speed test analyses of minor substances in the scientific field of biochemistry, analytical chemistry and the like or in the medical field.

REFERENCE SIGNS LIST

1 Analysis tool
2 Main body of microanalysis device
10, 70, 80 Main body of analysis tool
12 Attachment section
13 Mount surface
14a, 14b, 14c Inner surface
15a, 15b, 15c Projection
17a, 17b, Concave section
19 Counterbore section
20 Bottom surface
21 Notch section
30, 90 Micro flow path chip
31 Flat plate
32 Film
34a, 34b Flow path
35a, 35b, 35c, 35d Through-hole
38a, 38b Plate spring
39a, 39b Convex section
41 Knob section
42 Bottom surface
50 Heat block
60 Optical unit
71 concave section
81 Retaining section
82a, 83b Through-hole
91a, 91b Convex section

The invention claimed is:

1. An analysis tool used in an analysis system provided with the analysis tool including a micro flow path, a heat exchanging block capable of heating and cooling and an optical unit capable of emitting and receiving analytical light, the system in which light is radiated onto a sample located at a predetermined position in the micro flow path in a state where temperature of the micro flow path is controlled to be at a predetermined value and the analytical light from the sample is detected, the analysis tool comprising:
a micro flow path chip made of resin and in which the micro flow path is formed in an inside of the micro flow path chip; and
a main body of the analysis tool that holds the micro flow path chip in a detachably attached manner, wherein:
the micro flow path is formed so as to cross an optical path of the light radiated from an analytical light emitting section of the optical unit in a state where the analysis tool is arranged on the heat exchanging block, and on a mount surface of the main body of the analysis tool onto which the micro flow path chip is to be mounted, a clearance section is formed in a range of the mount surface corresponding to a trajectory where the predetermined position in the micro flow path moves when the micro flow path is attached to the main body of the analysis tool, to prevent the predetermined position in the micro flow path from contacting with the mount surface.

2. The analysis tool as in claim 1, wherein the clearance section is a formation of a notch.

3. The analysis tool as in claim 1, wherein the clearance section is a concave with flat bottom which is parallel to the mount surface.

4. A microanalysis system comprising the analysis tool as in claim 1.

* * * * *